US009469832B2

(12) United States Patent
Mena Mas

(10) Patent No.: US 9,469,832 B2
(45) Date of Patent: Oct. 18, 2016

(54) METHOD AND APPARATUS FOR PROVIDING A PHOTOBIOREACTOR

(76) Inventor: Jacinto Fernando Mena Mas, Amposta (ES)

(*) Notice: Subject to any disclaimer, the term of this patent is extended or adjusted under 35 U.S.C. 154(b) by 1616 days.

(21) Appl. No.: 12/710,552

(22) Filed: Feb. 23, 2010

(65) Prior Publication Data
US 2010/0178686 A1 Jul. 15, 2010

(30) Foreign Application Priority Data

Nov. 10, 2008 (ES) .................................. 200803197

(51) Int. Cl.
C12N 1/20 (2006.01)
C12N 1/12 (2006.01)
C12M 1/00 (2006.01)
C12M 1/12 (2006.01)
C12M 1/06 (2006.01)

(52) U.S. Cl.
CPC ............. C12M 21/02 (2013.01); C12M 23/06 (2013.01); C12M 27/06 (2013.01)

(58) Field of Classification Search
CPC .... C12M 21/02; C12M 27/06; C12M 23/06; C12M 21/12; C12M 23/18; C12M 23/26; C12M 29/22; C12M 27/20; C02F 3/28; C02F 3/32; Y02W 10/37; Y02E 50/343; Y02E 50/17; Y10S 210/906; Y02P 20/582
USPC ......... 435/257.1, 292.1, 252.1, 254.1; 47/1.4
See application file for complete search history.

(56) References Cited

U.S. PATENT DOCUMENTS

| 7,682,821 | B2 * | 3/2010 | Woods et al. .............. 435/292.1 |
| 2005/0115893 | A1 * | 6/2005 | Brune et al. .................. 210/602 |
| 2005/0260553 | A1 * | 11/2005 | Berzin .............................. 435/3 |
| 2007/0048848 | A1 * | 3/2007 | Sears ............................. 435/134 |
| 2008/0153080 | A1 * | 6/2008 | Woods et al. ..................... 435/4 |
| 2008/0178739 | A1 * | 7/2008 | Lewnard et al. ............... 95/186 |
| 2009/0011492 | A1 * | 1/2009 | Berzin ....................... 435/257.1 |

* cited by examiner

Primary Examiner — William H Beisner
Assistant Examiner — Danielle Henkel
(74) Attorney, Agent, or Firm — Marcus C. Dawes; Daniel L. Dawes

(57) ABSTRACT

The present invention provides for a photobioreactor for the cultivation of photosynthetic microorganisms and comprises a hydraulic circuit through which an aqueous solution containing culture of at least one type of photosynthetic organism circulates and gets exposed to a light source. The photobioreactor also comprises a means for feeding carbon dioxide into the system, a means for oxygen degasification, and a means for injecting nutrients into the system. The hydraulic circuit is comprised of two open receiving channels at the same relative elevation, a set of transparent or translucent tubes which connect receiving channels to each other, and at least one fluid moving device to move the fluid from the first to the second receiving channels through the tubes. Each receiving channel also comprises a dam which assists in maintaining two different surface levels of the aqueous solution within the upstream and downstream portions of each receiving channel.

8 Claims, 6 Drawing Sheets

METHOD AND APPARATUS FOR PROVIDING A PHOTOBIOREACTOR

BACKGROUND OF THE INVENTION

1. Field of the Invention

The invention relates to the field of microalgae and cyanobacteria, specifically how microalgae and cyanobacteria may be cultivated to produce biofuels, food for humans and animals, organic fertilizers or pharmaceutical products.

2. Description of the Prior Art

Due to the increasing costs of fossil fuels as well as its negative impact for the environment (e.g. climate change) there is a growing interest for the use of biofuels such as biodiesel and bioethanol. So far, these biofuels have been obtained from traditional oleaginous and cellulose rich feedstock. However, these traditional crops are not cost effective and the biofuel production yield is not high enough to compete with petroleum and its derivates. Therefore, the production of biofuels from traditional crops may lead to negative side effects such as intolerable rises in food prices and other global issues.

One of the most promising solutions to solve the fossil fuel scarcity and its associated environmental issues is the production of biofuels from microalgae which are single cell photoautotrophic microorganisms. Photoautotrophic organisms (usually plants) carry out photosynthesis to acquire energy from sunlight to convert carbon dioxide and water into organic materials to be used in cellular functions such as biosynthesis and respiration. Importantly, single cell microalgae living in an aqueous solution transform light into chemical energy much more efficiently than any other organism due to their greater access to carbon dioxide and dissolved minerals. In addition, single cell microalgae are able to store lipids in higher density than any other plant or multi-celled organism which requires time, energy and nutrients to build support structures such as roots and stalks, light collector structures such as leaves, and lipid storing organs such as seeds. Therefore, to produce biofuels from microalgae presents the following advantages with respect conventional crops, if cultivated at a large scale:

- Production yields are 30 to 100 times higher for microorganisms than any other known traditional crop.
- Microalgae can grow in soils and tolerate water that is not useful for conventional agriculture. They can even tolerate the use of waste water and saltwater.
- During its growth, enormous amounts of carbon dioxide as well as other contaminant gases are captured. In addition, vast amounts of oxygen are produced and liberated to the atmosphere.
- Microalgae are single cell organisms that convert sunlight into chemical energy through photosynthesis:

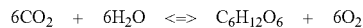

Microalgae and cyanobacteria are the planet's most abundant organisms, having adapted to extreme conditions such as polar and volcanic environments. They constitute the core of the trophic chain that sustains life on Earth as well as of the natural carbon cycle. They produce 80% of the planet's biomass (phytoplankton).

Some algae and cyanobacteria mass concentrations of lipids that may achieve proportions in the range of 60-70% by weight on a dry basis. Therefore, they are ideal to produce biodiesel. In addition, algae constitute an effective and powerful carbon sink. It has been demonstrated that 100 tons of algae biomass will capture 170 tons of carbon dioxide.

In addition to light, carbon dioxide and water, photosynthesis requires inorganic salts which include essential elements such as nitrogen, phosphorous, iron and in some cases, silicon. The optimal temperature for microalgae growth is between 20 and 30° C. Therefore, to cultivate microalgae and cyanobacteria, the following is required:

- An aqueous media containing the algal culture, which can be fresh water, brackish water or saltwater depending on the organism type.
- A light source in order to develop the photosynthetic process.
- A carbon dioxide source to enhance the photosynthetic process.
- A system to extract the oxygen produced during the photosynthesis.
- Nutrients (mineral salts).
- A system to move or circulate the aqueous media containing the algal culture to enhance the photosynthesis.

Today, there are two main types of photobioreactors to grow microalgae on a large scale:

Raceways or open ponds. These systems are very simple. They are composed of a circulating pond or a set of circulating channels open to the atmosphere in which the aqueous solution circulates while capturing the sunlight. The biggest advantage of these photobioreactors is that they are very economical. However, open photobioreactors do not easily sustain the conditions for desired microalgae and cyanobacteria growth because the conditions of the algal culture can vary substantially over time due to water evaporation. In addition production is affected by contamination with unwanted algae and microorganisms that are deposited on the algal culture.

Closed photobioreactors have been developed in many different typologies to overcome the issues found in open ponds. Closed photobioreactors are based on closed hydraulic circuits, mostly tubular, through which the algal culture circulates. This type of system allows more intensive algae growth, requires less land surface and does not present contamination risks. However, with this technology, the oxygen produced during the photosynthesis, which is toxic to the algae and bacteria, may become an issue and might be hard to eliminate. Additionally, the cost of installation is around ten times higher than the cost of raceway photobioreactors. Due to the high costs, closed photobioreactors are not yet economically viable.

Current photobioreactors present important limitations to producing microalgae and cyanobacteria at a large scale. Whereas some of them require enormous amounts of energy to operate, others present prohibitive construction, installation and maintenance costs.

Today, the bottleneck for the production of massive amounts of microalgae and cyanobacteria is the photobioreactor itself. What is needed is a developed photobioreactor that makes it technically and economically feasible to produce microalgae and cyanobacteria on a large scale and ultimately makes producing biofuels competitive with that of fossil fuels.

BRIEF SUMMARY OF THE INVENTION

The illustrated embodiments of the invention respond to the specific need for mass, cost-effective microalgae and cyanobacteria biomass production. The illustrated embodiments of the invention are based on a concept which offers the advantages of both raceway and closed tubular photobioreactors, namely the low costs of construction, operation and maintenance for the open raceway technology and the advantageous features of the closed photobioreactors (i.e. high production rates and biological safety). The illustrated embodiments of the invention respond to the specific need for an economically viable mass production of biofuels. The illustrated embodiments of the invention include a closed photobioreactor which can operate in a continuous manner either in an outdoor or indoor environment.

In particular, one of the illustrated embodiments of the invention comprises a novel photobioreactor which comprises a hydraulic circuit through which the aqueous solution containing the culture with at least one type of photosynthetic organism circulates and gets exposed to the light source, a carbon dioxide feeding system, a zone to extract the oxygen from the aqueous solution, and a nutrient feeding system.

In one particular embodiment, the hydraulic circuit is comprised of two receiving channels in which the aqueous solution containing the algal/bacterial culture is exposed to the atmosphere, where both receiving channels are at the same elevation where a set of transparent or translucent tubes connect the first and the second receiving channels, and where at least one fluid moving device moves the aqueous solution from the first to the second receiving channel through the transparent or translucent tubes.

In another embodiment, the present invention comprises a hydraulic circuit open to atmospheric pressure in which the algal/bacterial culture may be protected from external pollution since the photosynthesis reaction occurs within and along the transparent tubes. As a result, in order to protect the algal/bacterial culture from external pollution, it is only necessary to cover the receiving channels, which surface is an insignificant portion with respect to the total surface of the photobioreactor. In addition, since the system is closed to contamination, it is very straightforward and cost effective to eliminate the oxygen and to feed the nutrients and carbon dioxide into it.

The oxygen concentration of the aqueous solution increases as it passes through the tubes where photosynthesis takes place. Thus, the length and diameter of the transparent or translucent tubes are calculated to predetermined levels in each application according to well understood design principles in order to avoid toxic oxygen concentrations. This generated oxygen is then eliminated in the next receiving or downstream channel.

Because the system is an open hydraulic system (i.e. at atmospheric pressure), moving the algal/bacterial solution throughout the photobioreactor is straightforward and inexpensive. In one embodiment, the fluid moving device induces a difference in the surface level between the sides of the moving device. In addition, the same device may help to eliminate the oxygen from the algal/bacterial solution (i.e. degasification). The fluid moving device may be a rotary direct lift device such as a paddle wheel, noria, scoop wheel, etc. which may or may not incorporate perforated blades to enhance degasification.

In one embodiment, each receiving channel includes at least one fluid moving device.

In another preferred embodiment, carbon dioxide and nutrients are fed into the culture from both receiving channels simultaneously.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 122 The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
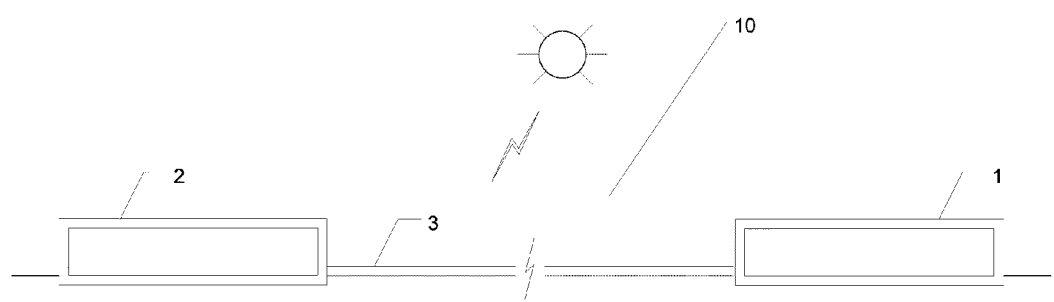
FIG. 1 is lateral broken-away view of a photobioreactor illustrating one embodiment of the present invention.

Turning to FIG. 1, one of the illustrated embodiments of the invention provides for a tubular photobioreactor 10 open to atmospheric pressure which comprises a horizontal tube set 3 disposed between a first receiving channel 1 and a second receiving channel 2 designed for massive algal/bacterial production. An aqueous solution contained within the receiving channels 1, 2 is circulated by a first fluid moving device 11 and a second fluid moving device 21 respectively as best seen in FIGS. 2 and 7.

Figure 2:
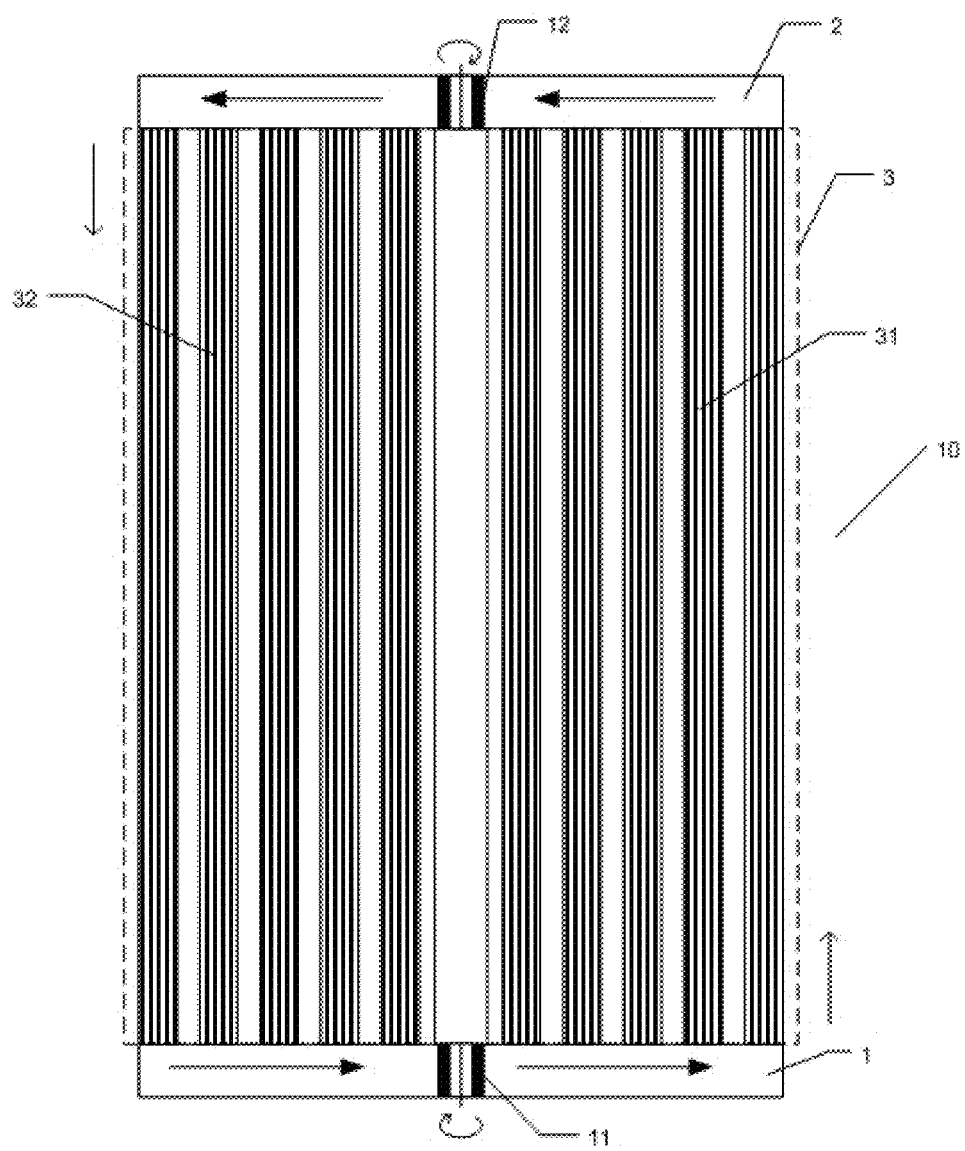
FIG. 2 is top view of the photobioreactor shown in FIG. 1.
Figure 3:
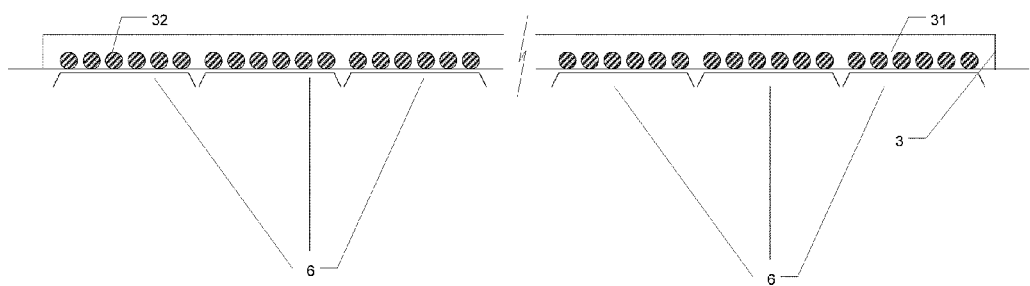
FIG. 3 is a cross sectional, broken-away view of the photobioreactor in which a portion of the wall on the side of one of the receiving channels as well as the cross section of the tubes are shown in order to illustrate the interior portion of the photobioreactor.
Figure 4:
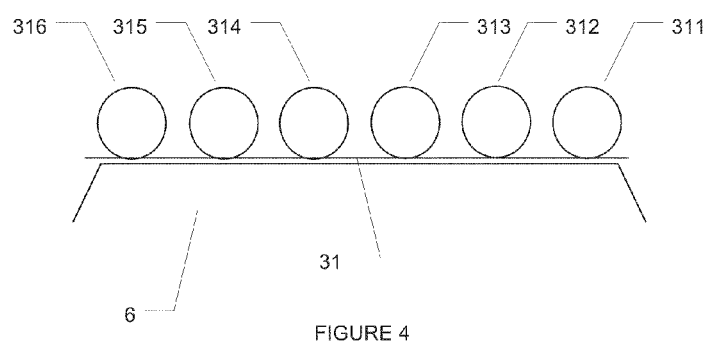
FIG. 4 is a detailed magnified view of a portion of the photobioreactor shown in FIG. 3.
Figure 7:
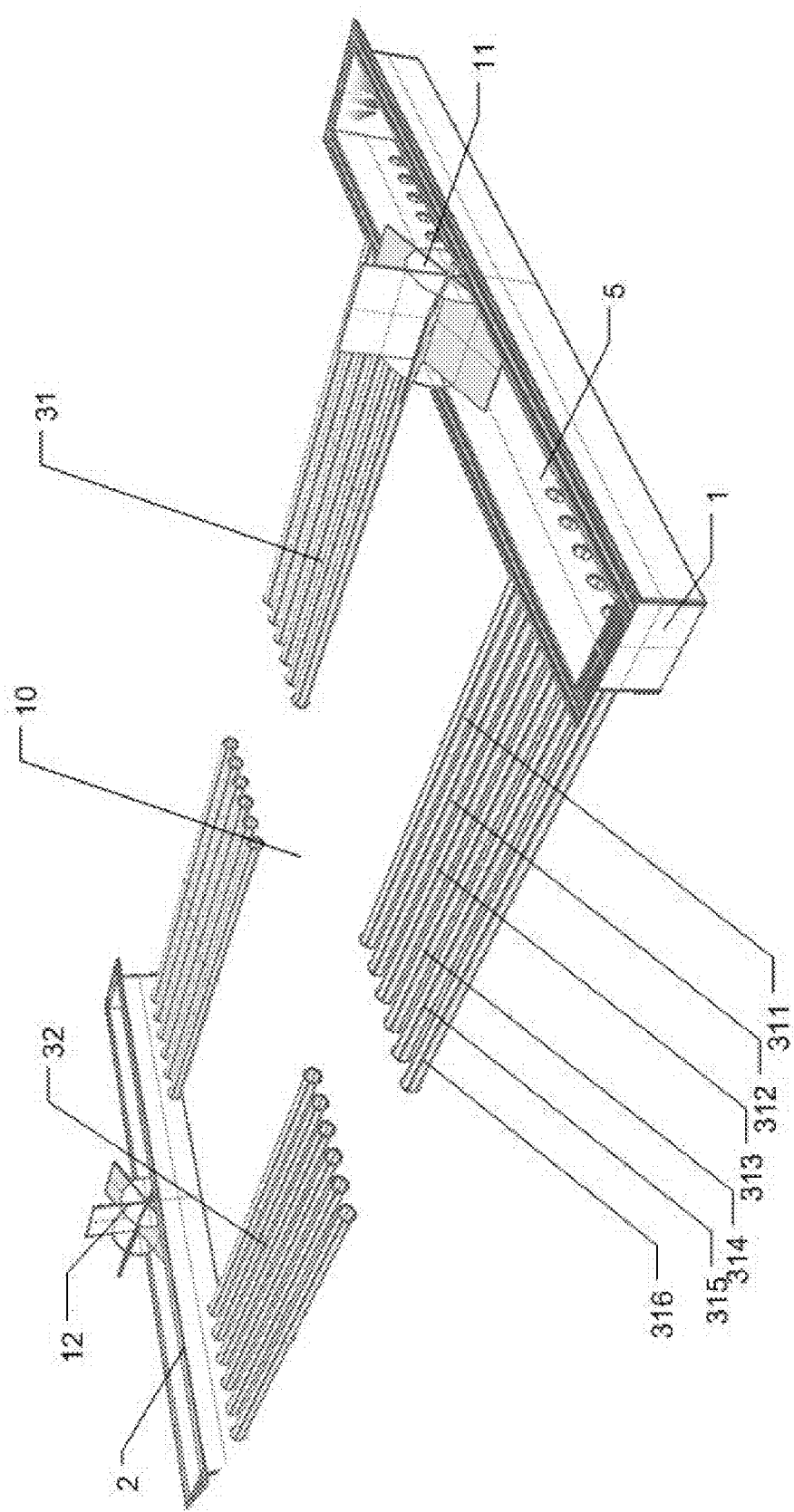
FIG. 7 is a perspective view of the photobioreactor shown in FIGS. 1 and 2.

In one embodiment of the invention, the horizontal tube set 3 of the photobioreactor 10 comprises a plurality of subsets or "ramps" 31, 32 of tubes as seen in FIGS. 2, 3 and 7. For definitional purposes, ramps comprising the right-hand hemisphere of the horizontal tube set 3 as seen in FIG. 2 are denoted with reference numeral 31, while ramps comprising the left-hand hemisphere of the horizontal tube set 3 are denoted with reference numeral 32. Each ramp 31, 32 in turn comprises a plurality of tubes 311, 312, 313, 314, 315, 316 seen in the magnified cross sectional view of FIG. 4. Each individual tube 311-316 is preferably comprised of low-density polyethylene (LDPE) plastic with a thickness preferably between 800 and 2000 gauges (1 gauge=0.01 mil). Each tube 311-316 is placed horizontally and parallel to each other within each ramp 31, 32. Each tube 311-316 is also transparent or translucent enough to become an efficient sunlight collector. The tubes 311-316 are assembled in sets of six within each ramp 31, 32, however it is to be expressly understood that each ramp 31, 32 may contain fewer or additional tubes 311-316 than from what is seen in FIG. 4 without departing from the original spirit and scope of the invention.

Each ramp 31, 32 is placed on a portion of leveled ground 6 which is covered by a plastic film (not shown). The plastic film is black or opaque on the bottom to prevent new vegetation growth beneath the ramps 31, 32, and white on the top to enhance light reflection along the surface area of the leveled ground 6 beneath the ramps 31, 32.

Each end of the plurality of tubes 311-316 within each of the plurality of ramps 31, 32 are coupled individually to the first receiving channel 1 and second receiving channel 2 respectively as best seen in FIGS. 2 and 7. The receiving channels 1, 2 collect the aqueous solution which contains an algal/bacterial culture 5. The aqueous solution and algal/bacterial culture 5 travel in the same direction within each of the ramps 31, 32, specifically from the first receiving channel 1 to the second receiving channel 2 in the right-hand hemisphere of ramps 31, and from the second receiving channel 2 to the first receiving channel 1 in the left-hand hemisphere of ramps 32.

As the algal/bacterial culture 5 travels through the horizontal tube set 3, incoming solar light crosses into the transparent tubes 311-316 within each ramp 31, 32 and causes a photosynthesis reaction with the algal/bacterial culture 5. Oxygen that is generated during the photosynthesis reaction along the tubes 311-316 is carried to the receiving channels 1, 2 where it is eliminated by degasification. Carbon dioxide and other nutrients are fed into the receiving channels 1, 2 which prepare the algal/bacterial culture 5 for a subsequent photosynthetic process to take place while it travels through the opposing set of ramps 31, 32 in the opposite direction towards the other receiving channel 1, 2 in which it came. Thus it can be seen that the receiving channels 1, 2 and ramps 31, 32 work together to form a unidirectional loop or circuit, namely from the first receiving channel 1 through the right-hand hemisphere of ramps 31 to the second receiving channel 2, and then back to the first receiving channel 1 through the left-hand hemisphere of ramps 32. In order to circulate the aqueous solution through the loop, each of the receiving channels 1, 2 drives the aqueous solution with an inbuilt fluid moving device 11, 12. Each fluid moving device 11, 12 may be any apparatus known in the art for moving a fluid such as a paddle wheel, noria, scoop wheel, or any other similar apparatus. The fluid moving devices 11, 12 move the aqueous solution along the receiving channels 1, 2 in the direction of the arrows shown in FIG. 2, namely from one set of tubes to the other set of tubes so that the aqueous solution may be driven towards the other respective receiving channel 1, 2.

According to the above description, it is preferred that the number of ramps 31, 32 be even. In the preferred illustrated embodiment shown in FIGS. 2, 3, and 7, the photobioreactor 10 comprises at least ten ramps 31, 32, five ramps 31 flowing into the second receiving channel 2, and five ramps 32 flowing into the first receiving channel 1. The length of the tubes 311-316 are preferably between 50 to 80 meters. Additionally, it is preferred the diameter of the tubes 311-316 to be between of 12.5 and 15 centimeters. It is to be expressly understood however that the length and diameter of each of the tubes 311-316 may be different from what is disclosed above and may be varied in order to avoid oxygen levels from reaching toxic conditions within the algal/bacterial culture 5. The disclosed parameters of the tubes 311-316 may also be adjusted during the photosynthesis process according to changing microalgae or cyanobacteria growing conditions.

The receiving channels 1, 2 may be built of different materials such as HDPP, HDPE, polyester, or a combination thereof. The dimensions of the receiving channels 1, 2 are such that enough surface area is present to allow for degasification. Additionally, the depth of the aqueous solution in the downstream portion 8 of the receiving channels 1, 2 is at least a few centimeters greater than that the diameter of the tubes 311-316. In another embodiment, the receiving channels 1, 2 are built from brick, although this is not the most optimal solution. In yet another embodiment, the receiving channels 1, 2 may serve as sun collectors in addition to the tubes 311-316 if covered with transparent materials known in the art (not shown). In this embodiment, the photobioreactor 10 does not comprise any dark areas in order to allow the algal/bacterial solution 5 to react with the incoming solar light throughout its entire circulation through the photobioreactor 10.

Figure 5:
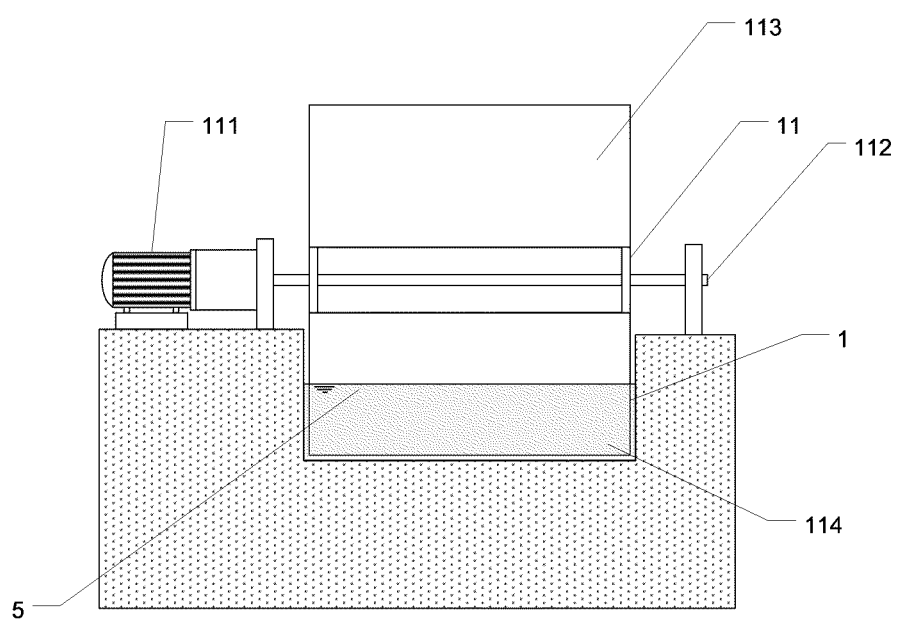
FIG. 5 is cross sectional view of a receiving channel in which a fluid moving device, for example a paddle wheel, can be observed.

The fluid moving device 11, 12 is disposed in the center point of each receiving channel 1, 2 as seen in FIGS. 2 and 7. In one preferred embodiment, the fluid moving device 11, 12 comprises a plurality of radially disposed blades 113, 114 that are rotated by an electric motor 111 as best seen in FIG. 5. The electric motor 111 may be any type or model of electric motor now known or later devised and may have a power capacity as little as one horsepower (HP). Alternatively, the motor 111 may not be electric at all but rather a traditional gasoline or diesel motor as is known in the art. The motor 111 is coupled to the fluid moving device 11, 12 via a driveshaft 112, or other similar speed variation means through which the revolutions per minute of the fluid moving device 11, 12 may be controlled in order to achieve an optimal fluid velocity along the receiving channels 1, 2. The optimal fluid velocity preferably avoids algal/bacterial culture deposition on the internal walls of the various components of the photobioreactor 10 including the receiving channels 1, 2 and ramps 31, 32.

Figure 6:
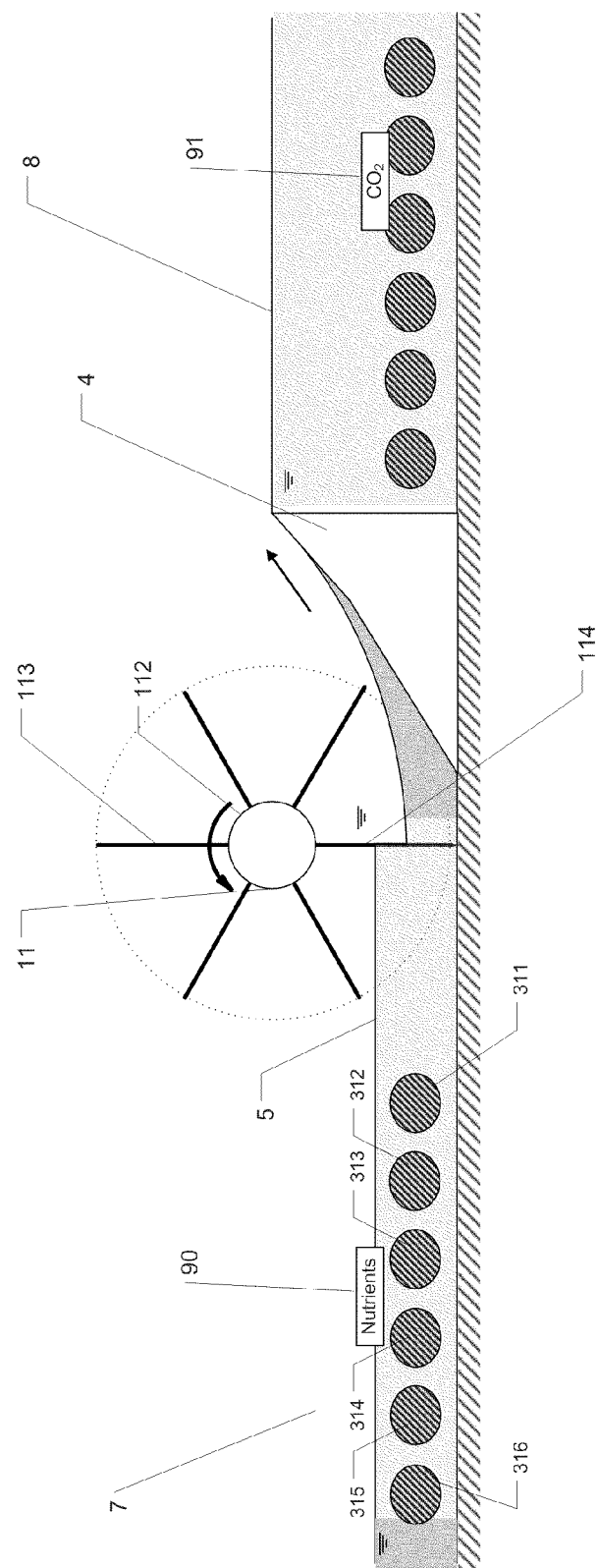
FIG. 6 is lateral view of the fluid moving device within one of the receiving channels shown in FIG. 5.

The pitch of the plurality of blades 113, 114 of the fluid moving devices 11, 12 are such that, when the fluid moving device 11, 12 is in motion within the algal/bacterial culture 5, a difference is created in the fluid level between an upstream portion 7 and an downstream portion 8 of the receiving channels 1, 2 as best seen in FIG. 6. For definitional purposes, "upstream" refers to the flow of the aqueous solution and algal/bacterial culture 5 before it makes contact with the fluid moving device 11, 12, while "downstream" refers to the flow of the aqueous solution and algal/bacterial culture 5 after it has made contact with the fluid moving device 11, 12. The difference in fluid levels between the upstream portion 7 and the downstream portion 8 of the receiving channels 1, 2 is maintained by a substantially wedged shaped dam 4. As the aqueous solution and algal/bacterial culture 5 enter into the receiving channels 1, 2 via the plurality of ramps 31, 32 and their corresponding tubes 311-316, the algal/bacterial culture 5 collects in the upstream portion 7 of the receiving channel 1, 2. As the fluid moving device 11, 12 is set into a counterclockwise motion indicated by the arrow seen in FIG. 6, the algal/bacterial solution 5 is drawn to the plurality of blades 113, 114. As the fluid moving device 11, 12 continues to spin, the plurality of blades 113, 114 continually push the algal/bacterial culture 5 up and over the dam 4 and into the downstream portion 8 of the receiving channel 1, 2. The upstream surface of dam 4 may be curved to assist in the formation of wavelets in the culture 5, like a sloped beach, as it is pushed by the blades 113, 114, which wavelets then crest or spill over the top of dam 4 to the downstream side. The dam 4 not only prevents the algal/bacterial culture 5 that has entered the downstream portion 8 from re-entering the upstream portion 7 of the receiving channel 1, 2, but it also prevents waves that have reflected off the inner walls of the receiving channel 1, 2 from coming back and opposing the motion of the plurality of blades 113, 114 and thus unnecessarily increasing the load on the motor 111. Because the fluid level in the downstream portion 8 is higher than in upstream portion 7, a sufficient fluid pressure differential is created which moves the aqueous solution and algal/bacterial culture 5 out of the original receiving channel 1, 2 and along the ramps 31, 32 towards the opposing receiving channel 1, 2 where the entire process is repeated. With a fluid moving device 11, 12 located in both the first and second receiving channels 1, 2 respectively, it is ensured that a higher fluid level is maintained within the downstream portion 8 of each receiving channel 1, 2 and it is in this manner that circulation of the algal/bacterial culture 5 throughout the entirety of the photobioreactor 10 is achieved for as long as the fluid moving devices 11, 12 are in operation.

In addition to moving the algal/bacterial culture 5 within the aqueous solution, each fluid moving device 11, 12 also facilitates in the gas exchange (i.e. the release of oxygen and the capture of carbon) as well as in the homogenous mixing of the algal/bacterial culture 5 with nutrients. As the algal/bacterial culture 5 is pushed along the transparent tubes 311-316, the oxygen concentration increases as the photosynthesis reactions take place. As the algal/bacterial culture 5 enters the receiving channels 1, 2, degasification of oxygen takes place due to the turbulence created by the fluid moving device 11, 12 as it makes contact with the algal/bacterial culture 5. Additionally, each of the receiving channels 1, 2 may comprise a means for injecting nutrients 90 as well as pure carbon dioxide or carbon dioxide streams 91 into the algal/bacterial culture 5 as it travels through the receiving channels 1, 2. In one embodiment, it is preferred that the nutrients 90 are injected into the receiving channels 1, 2 just before the algal/bacterial culture 5 makes contact with the fluid moving device 11, 12 as seen in FIG. 6 so as to take maximum advantage of the turbulence and mixing effect created by the plurality of blades 113, 114. Therefore, in one embodiment, some or all of the plurality of blades 113, 114 may include perforations or be made from a metal mesh so as to more effectively mix the algal/bacterial culture 5 with the nutrients and/or to aid in the exchange of gases. Preferably, the carbon dioxide is injected into the algal/bacterial culture 5 in the downstream portion 8 of the receiving channels 1, 2 with a carbon dioxide injecting device 91 located near or at the beginning of each tube 311-316 in order to minimize losses.

The velocity of the aqueous solution and the algal/bacterial culture 5 as it travels within the photobioreactor 10 is regulated by varying the rotation speed of the fluid moving device 11, 12 via the electric motor 111, or by operating only one of the two fluid moving devices 11, 12 contained within the photobioreactor 10.

While it is thus apparent that the preferred embodiment shown and described provides certain advantages, many of the advantages of the present invention can nevertheless be realized in other configurations, and it will be appreciated that various modifications, changes and adaptations can be made, all of which are intended to be comprehended within the meaning and range of equivalents of the appended claims.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A photobioreactor comprising:
   at least two receiving channels;
   a plurality of transparent or translucent tubes disposed between the at least two receiving channels, wherein each of the plurality of transparent or translucent tubes are directly and fluidly coupled to each of the two receiving channels at both ends;

at least one fluid moving device disposed within each of the at least two receiving channels;

a dam disposed within each of the at least two receiving channels and immediately and adjacently downstream of the at least one fluid moving device disposed within each of the at least two receiving channels; and at least one type of photosynthetic organism mixed with an aqueous solution capable of flowing through the at least two receiving channels and plurality of transparent or translucent tubes, wherein the dam provides a constant fluid pressure differential over the plurality of transparent and translucent tubes disposed downstream of the at least one fluid moving device.

2. The photobioreactor of claim 1 wherein the at least one fluid moving device disposed within each of the at least two receiving channels comprises means for circulating the photosynthetic organism mixed with the aqueous solution in substantially one direction through the at least two receiving channels and plurality of transparent or translucent tubes.

3. The photobioreactor of claim 1 wherein the at least one fluid moving device disposed within each of the at least two receiving channels comprises means for releasing oxygen gas contained within the photosynthetic organism mixed with the aqueous solution and capturing carbon dioxide gas within the photosynthetic organism mixed with the aqueous solution.

4. The photobioreactor of claim 1 where the at least one fluid moving device in each of the at least two receiving channels comprises means for directing the aqueous solution over the dam disposed in each of the at least two receiving channels and wherein the dam comprises means for maintaining a surface level difference of the aqueous solution between the upstream and downstream portions of the at least two receiving channels, wherein the at least two receiving channels and fluid moving device are configured to provide a uni-directional fluid flow over the dam.

5. The photobioreactor of claim 1 in which the at least one fluid moving device within each of the at least two receiving channels is a rotary direct lift device such as a paddle wheel.

6. The photobioreactor of claim 1 wherein the at least two receiving channels are open to atmospheric pressure.

7. The photobioreactor of claim 1 wherein the at least two receiving channels comprise a transparent or translucent cover disposed over their entire surface area, wherein the at least two receiving channels remain open to atmospheric pressure.

8. The photobioreactor of claim 1 further comprising means for injecting carbon dioxide gas into at least one of the receiving channels.

* * * * *